(12) United States Patent
Yin et al.

(10) Patent No.: US 7,754,500 B2
(45) Date of Patent: *Jul. 13, 2010

(54) ASYMMETRICALLY BRANCHED POLYMER CONJUGATES AND MICROARRAY ASSAYS

(75) Inventors: Ray Yin, Newark, DE (US); Dujie Qin, Abingdon, MD (US); Jing Pan, Newark, DE (US)

(73) Assignee: ANP Technologies, Inc., Newark, DE (US)

( * ) Notice: Subject to any disclaimer, the term of this patent is extended or adjusted under 35 U.S.C. 154(b) by 16 days.

This patent is subject to a terminal disclaimer.

(21) Appl. No.: 10/993,474

(22) Filed: Nov. 22, 2004

(65) Prior Publication Data
US 2006/0041058 A1  Feb. 23, 2006

Related U.S. Application Data

(60) Provisional application No. 60/523,692, filed on Nov. 21, 2003, provisional application No. 60/580,728, filed on Jun. 21, 2004.

(51) Int. Cl.
*G01N 33/553* (2006.01)
*A61K 31/74* (2006.01)

(52) U.S. Cl. ............ 436/525; 436/528; 436/529; 436/546; 424/78.17; 435/975

(58) Field of Classification Search ............ 424/78.17; 435/975; 436/525, 528, 529, 546
See application file for complete search history.

(56) References Cited

U.S. PATENT DOCUMENTS

| 4,289,872 | A |   | 9/1981  | Denkewalter et al. |
|-----------|---|---|---------|--------------------|
| 4,360,646 | A | * | 11/1982 | Denkewalter et al. ........ 525/420 |
| 4,507,466 | A |   | 3/1985  | Tomalia et al. |
| 4,558,120 | A |   | 12/1985 | Tomalia et al. |
| 4,568,737 | A |   | 2/1986  | Tomalia et al. |
| 4,587,329 | A |   | 5/1986  | Tomalia et al. |
| 4,599,400 | A |   | 7/1986  | Tomalia et al. |
| 4,631,337 | A |   | 12/1986 | Tomalia et al. |
| 4,690,985 | A |   | 9/1987  | Tomalia et al. |
| 4,694,064 | A |   | 9/1987  | Tomalia et al. |
| 4,713,975 | A |   | 12/1987 | Tomalia et al. |
| 4,737,550 | A |   | 4/1988  | Tomalia |
| 4,857,599 | A |   | 8/1989  | Tomalia et al. |
| 5,338,532 | A |   | 8/1994  | Tomalia et al. |
| 5,393,795 | A |   | 2/1995  | Hedstrand et al. |
| 5,393,797 | A |   | 2/1995  | Hedstrand et al. |
| 5,482,830 | A |   | 1/1996  | Bogart et al. |
| 5,527,524 | A |   | 6/1996  | Tomalia et al. |
| 5,631,329 | A |   | 5/1997  | Yin et al. |
| 5,714,166 | A |   | 2/1998  | Tomalia et al. |
| 5,731,095 | A |   | 3/1998  | Milco et al. |
| 5,773,527 | A |   | 6/1998  | Tomalia et al. |
| 5,861,319 | A |   | 1/1999  | Lin et al. |
| 5,898,005 | A |   | 4/1999  | Singh et al. |
| 5,919,442 | A |   | 7/1999  | Yin et al. |
| 6,020,457 | A |   | 2/2000  | Kllmash et al. |
| 6,043,336 | A |   | 3/2000  | Miller et al. |
| 6,083,708 | A |   | 7/2000  | Singh et al. |
| 6,121,056 | A |   | 9/2000  | Moll, III et al. |
| 6,274,713 | B1 |   | 8/2001 | Sieving et al. |
| 6,632,889 | B1 |   | 10/2003 | Yin et al. |
| 6,716,450 | B1 | * | 4/2004 | Yin et al. .................. 424/451 |
| 6,743,581 | B1 |   | 6/2004 | Von-Dinh et al. |
| 6,773,928 | B1 |   | 8/2004 | Yin et al. |
| 7,217,457 | B2 |   | 5/2007 | Elaissari et al. |
| 2002/0098163 | A1 | * | 7/2002 | Zeng et al. ............... 424/85.1 |
| 2002/0155523 | A1 | * | 10/2002 | Sparks .................. 435/68.1 |
| 2003/0026764 | A1 |   | 2/2003 | Griffiths |
| 2003/0045810 | A1 | * | 3/2003 | Borkowski ............ 600/562 |
| 2003/0143596 | A1 |   | 7/2003 | Bentley et al. |
| 2003/0203915 | A1 |   | 10/2003 | Fang et al. |
| 2004/0038378 | A1 | * | 2/2004 | Hellinga et al. ......... 435/252.3 |

FOREIGN PATENT DOCUMENTS

| EP | 1151995 | 11/2001 |
|----|---------|---------|
| WO | WO00/43044 | 7/2000 |
| WO | WO01/28524 | 4/2001 |
| WO | WO01/52979 | 7/2001 |
| WO | WO02/087508 | 11/2002 |
| WO | WO03/020701 | 3/2003 |
| WO | WO03/086282 | 10/2003 |

OTHER PUBLICATIONS

Webster's II dictionary, p. 1276.*

* cited by examiner

*Primary Examiner*—Milton I Cano
*Assistant Examiner*—Gennadiy Mesh
(74) *Attorney, Agent, or Firm*—MDIP LLC

(57) ABSTRACT

Asymmetrically branched polymers are combined with bioactive agents for a variety of purposes including drug delivery and conjugation to one member of a binding pair for use in an assay.

46 Claims, 7 Drawing Sheets

A

Random ABP

B

Regular ABP

At 100 ng/ml bot toxoid:

Assay configured without ABP

Assay configured with ABP

FIG. 7

ASYMMETRICALLY BRANCHED POLYMER CONJUGATES AND MICROARRAY ASSAYS

This Application claims the benefits of provisional Application US 60/523,692 filed on Nov. 21, 2003 and benefits of provisional Application US 60/580,728 filed on Jun. 21, 2004.

FIELD OF THE INVENTION

The present invention concerns the use of asymmetrically branched polymers in composite materials, such as conjugates, which can be employed in assay applications related to use in agriculture, environmental studies, diagnostics, drug monitoring, drug target screening, lead optimization, and therapeutics, and other materials, particularly those having biological activities and target recognition capabilities.

BACKGROUND OF THE INVENTION

Asymmetrically Branched Polymers

In recent years, a new class of polymers called dendritic polymers, including both Starburst dendrimers (or Dense Star polymers) and Combburst dendrigrafts (or hyper comb-branched polymers), have been developed and extensively studied in industrial and academic laboratories (Dendritic Molecules, edited by G R Newkome et al., VCH, Weinheim, 1996, and Dendrimers and Other Dendritic Polymers, edited by J M J Frechet and D A Tomalia, John Wiley & Sons, Ltd., 2001). These polymers often exhibit: (a) a well-defined core molecule, (b) at least two concentric dendritic layers (generations) with symmetrical (equal) branch junctures, and (c) exterior surface groups, as described in Tomalia's U.S. Pat. Nos. 4,435,548; 4,507,466; 4,568,737; 4,587,329; 5,338,532; 5,527,524; and 5,714,166, and the references therein.

These symmetrically branched dendrimers are also distinctively different from the previously prepared asymmetrically branched dendrimers (Denkewalter's U.S. Pat. Nos. 4,289,872; 4,360,646; and 4,410,688). The latter possess asymmetrical (unequal) branch junctures.

Both types of dendrimers can be produced by repetitive protecting and deprotecting procedures through either a divergent or a convergent synthetic approach. Since both symmetric and asymmetric dendrimers utilize small molecules as molecular building blocks for the cores and the branches, the molecular weights of these dendrimers are often precisely defined. In the case of lower generations, a single molecular weight dendrimer is often obtained.

Similar to dendrimers, Combburst dendrigrafts are also constructed with a core molecule and concentric layers with symmetrical branches through a stepwise synthetic method. In contrast to dendrimers, Combburst dendrigrafts or polymers are generated with monodisperse linear polymeric building blocks (Tomalia's U.S. Pat. No. 5,773,527 and Yin's U.S. Pat. Nos. 5,631,329 and 5,919,442). Moreover, the branch pattern is also very different from that of dendrimers. For example, Combburst dendrigrafts form branch junctures along the polymeric backbones (chain branches), while Starburst dendrimers often branch at the termini (terminal branches). Due to the utilization of living polymerization techniques, the molecular weight distributions (Mw/Mn) of these polymeric building blocks (core and branches) are often very narrow. As a result, Combburst dendrigrafts, produced through a graft-upon-graft process, are rather well defined with molecular weight distributions (Mw/Mn) often less than 1.2.

Although possessing well controlled molecular architecture, such as well defined size, shape, and surface functional groups, both dendrimers and dendrigrafts can only be produced through a large number of reiteration steps, making them only useful for esoteric academic studies rather than large scale commercial applications.

Dendrimers and dendrigrafts have been shown to possess unique carrier properties for bioactive molecules, as described in Tomalia's U.S. Pat. Nos. 5,338,532; 5,527,524; and 5,714,166 for Dense Star Polymers, and Yin's U.S. Pat. No. 5,919,442 for Hyper Comb-Branched Polymers. These unique properties (i.e., surface functional groups and interior void spaces) have been primarily attributed to the well-controlled, symmetrical dendritic architecture with predictable branching patterns (either symmetrical termini or polymeric chain branching) and molecular weights.

According to these teachings, random and regular, asymmetrically branched polymers (ran-ABP and reg-ABP) have long been considered as poor carrier materials. For example, a ran-ABP possesses: a) no core, b) functional groups both at the exterior and in the interior, c) variable branch lengths and patterns (i.e., termini and chain branches), and d) unevenly distributed interior void spaces. Although a reg-ABP possesses a core, the functional groups are both at the exterior and in the interior. Therefore, both ran-ABP and reg-ABP are generally considered to be unsuitable for carrying bioactive molecules.

The preparation of reg-ABP made of polylysine has been described, as illustrated in U.S. Pat. Nos. 4,289,872; 4,360,646; and 4,410,688.

The synthesis and mechanisms of ran-ABPs, such as made of polyethyleneimine (PEI), have been extensively studied (see G D Jones et al., J. Org. Chem. 9, 125 (1944), G D Jones et al., J. Org. Chem. 30, 1994 (1965), and C R Dick et al., J. Macromol. Sci. Chem., A4 (6), 1301-1314, (1970)).

The synthesis and characterization of random asymmetrically branched polymers, such as made of polyoxazoline, i.e., poly(2-methyloxazoline) and/or poly(2-ethyloxazoline), have been extensively studied by Litt (J. Macromol. Sci. Chem. A9(5), pp. 703-727 (1975)) and Warakomski (J. Polym. Sci. Polym. Chem. 28, 3551 (1990)).

Most of the prior art involved the utilization of polyethyleneimine polymers as coating materials to alter the characteristics of solid surfaces (i.e. changing charges, charge densities, and hydrophobicity). The coating aspects of polyethyleneimine polymers have been described in J Ness's U.S. Pat. No. 6,150,103 and K Moynihan's U.S. Pat. No. 6,365,349. Polyethyleneimines have also been tested as to carrying DNA molecules for gene transfection studies. However, the polymer was found to be cytotoxic.

Randomly branched poly(2-ethyloxazoline) has also been utilized to physically encapsulate protein molecules (U.S. Pat. No. 6,716,450). However, such an approach was not designed for the direct, covalent linking of ABP with bioactive materials for bioassays and drug delivery applications.

So far, none of the existing prior art has utilized modified ran-ABP and reg-ABP to carry bioactive materials for drug delivery and target recognition purposes, particularly for assay and microarray related applications, wherein transporting, anchoring, and orienting biologically active materials from a solution onto a solid surface all occur at the same time.

Assays and Microarrays

Since the completion of the human genome project, more and more researchers have realized that the elucidation of biological pathways and mechanisms at the protein level is actually far more important than at the genetic level. This is because the former is more closely related to different diseases and disease stages. With this strong demand push, a new forum called proteomics has recently become a major research focus for both industrial and academic researchers.

Currently, three major research tools have been employed in the proteomics research arena, primarily for the discovery, high throughput screening, and validation of new protein targets and drug leads. These tools include two dimensional (2-D) gel electrophoresis, mass spectrometry, and more recently, protein microarrays. In contrast to the lengthy 2-D gel procedures and tedious sample preparation (primarily separations) involved in mass spectrometry analysis, protein microarrays provide a fast, easy, and low-cost method to screen large amounts of proteins, as well as their functions. Therefore, microarrays are highly desired by proteomics researchers.

However, the protein-based microarray technology is far less developed than gene microarrays. The construction of a protein/antibody chip presents daunting challenges not encountered in the development of classical immunoassays or of DNA chips. In general, proteins are more sensitive to their environment than nucleic acids. The hydrophobicity of many membrane, glass, and plastic surfaces can cause protein denaturation, rendering the capture molecules inactive and resulting in lower sensitivity and higher noise-to-signal ratios. In other words, to construct a protein microarray, one must be able to overcome at least three major problems, protein denaturation, immobilization, and orientation.

For example, a protein molecule often folds into a three-dimensional structure in solution for and to maintain biological activity. On interaction with different solid surfaces, for example, during immobilization of proteins onto membranes, glass slides, or micro/nanoparticles, the three-dimensional structure of the protein molecule often collapses, thus losing biological activity. In addition, proteins often do not have the ability to adhere onto different surfaces.

To immobilize the protein molecule on a surface, a direct covalent linking reaction or an electrostatic interaction (physical adsorption) often has to be employed. Heterogeneous chemical reactions often are incomplete yielding undesired side products (i.e. incomplete modification of surfaces), and in some cases, also partially denatured proteins during different reaction stages.

The electrostatic interaction relies heavily on the isoelectric points of the proteins, as well as the pH of the buffer solutions.

Both approaches tend to give irreproducible results due to the complexity involved in these procedures. The lot-to-lot reproducibility is, therefore, very poor. As a result, there is a great interest in modifying solid substrates, but not the protein molecule itself. A variety of polymers, including polyethyleneimine polymers, have been utilized as coating materials to alter the characteristics of solid surfaces for the construction of protein arrays, as described by P Wagner et al. in U.S. Pat. No. 6,406,921.

So far, none of the prior art utilizes modified random and regular asymmetrically branched polymers as carriers for bioactive materials, particularly for the construction of assays and microarrays.

SUMMARY OF THE INVENTION

In one aspect, the present invention is directed to polymer conjugate materials comprising asymmetrically branched polymers (ABP) associated with desired materials (hereinafter called ABP conjugates), processes for preparing these polymers and conjugates, compositions containing the conjugates, and methods of using the conjugates and compositions.

Also included is an asymmetrically branched polymer associated with multiple units of carried material, and each with different properties and activities. Such conjugates may be formulated with acceptable carriers, diluents, and additives for use, for example, in biodetection, diagnostics, agriculture and pharmaceuticals.

The asymmetrically branched polymer conjugates are suitable for use in a variety of applications where specific delivery of bioactive materials is desired. In a preferred embodiment of the present invention, the random asymmetrically branched polymer conjugates are comprised of one or more asymmetrically branched polymers associated with one or more bioactive materials.

In another aspect of the invention, the asymmetrically branched polymer has either random or regular, asymmetrical branch junctures with a mixture of terminal and chain branching patterns.

In another aspect of the invention, the asymmetrically branched polymer has functional groups both at the exterior and in the interior.

In another aspect of the invention, the asymmetrically branched polymer has unevenly distributed void spaces.

In another aspect of the invention, the asymmetrically branched polymer is modified with at least one monomer capable of forming additional branches at a given time so that new material properties can be achieved, wherein the said modified polymer is defined as a modified asymmetrically branched polymer.

The modified asymmetrically branched polymers can be either obtained through chemically linked functional groups on regular asymmetrically branched polylysines or on random asymmetrically branched polyethyleneimines (commercially available from Aldrich, Polysciences, or BASF under the trade name, Luposal™).

The random asymmetrically branched polyoxazoline polymers can be prepared according to procedures described by M Litt (J. Macromol. Sci. Chem. A9(5), pp. 703-727 (1975)).

In another aspect of the invention, the asymmetrically branched polymer is further modified with functional groups, such as, but not limited to an —$NH_2$, —NHR, —$NR_2$, —$NR_3^+$, —COOR, —COOH, —COO—, —OH, —C(O)R, —C(O)$NH_2$, —C(O)NHR, or —C(O)$NR_2$ group, an aliphatic group, which can be branched, contain one or more double and/or triple bonds and/or may be substituted, an aromatic group, which may contain a plurality of rings, which may be fused or separated, the rings may be of varying size and/or may contain substituents, perfluorocarbon chains, saccharides, which may be of varying ring sizes, the rings may contain a heteroatom, such as a sulfur or nitrogen atom, and/or may be substituted, polysaccharides, containing two or more monomers, may be branched and/or may be substituted, and polyethylene glycols, wherein R can be any aliphatic or aromatic group, or a combination thereof, as defined herein.

The molecular weight of these non-modified and modified asymmetrically branched polymers can range from about 500 to over 5,000,000; preferably from about 500 to about 1,000,000; more preferably from about 1,000 to about 500,000; and more preferably from about 2,000 to about 100,000.

The preferred conjugates of the present invention include those where an asymmetrically branched polymer conjugate comprises at least one non-modified and/or modified asymmetrically branched polymer associated with at least one unit of at least one biologically active (bioactive) material. Some examples of biologically active materials are interleukins, interferons, T-helper cell CD4 molecule, $F_c$ receptor, acetylcholine receptor (AChR), T cell receptor for antigen, insulin receptor, tumor necrosis factor, granulocyte colony stimulating factor, hormone receptors, antibodies, antibody fragments, IgG molecules, $F_{ab}$ and other antibody derivatives that bind antigen, recombinant proteins, polypeptides, phage, phage fragments, DNA fragments, RNA fragments, hormones, such as insulin and hCG, enzymes, sialic acid, porphyrins, nucleotides, viruses, viral fragments and so on.

The instant invention also contemplates compositions comprising a plurality of polymers of interest encapsulating at least one biologically active molecule. A single species of polymer of interest or plural species of polymers can be used to form the encapsulating layer.

In one aspect of the invention, the non-modified and/or modified asymmetrically branched polymer-bioactive material conjugates can be utilized, for example, for the rapid detection of target molecules of interest, such as environmental pollutants, chemical and biological warfare agents, as well as for screening for drug targets and leads, and therapeutic drug and therapeutic effect monitoring.

In another aspect of the invention, the non-modified and/or modified asymmetrically branched polymer-bioactive material conjugates can be utilized, for example, for the rapid diagnosis of different cancers, tumors, pathological states and diseases, as well as for monitoring biomarker changes and protein profiling during clinical trials and therapeutic treatments.

In another aspect of the invention, the non-modified and/or modified asymmetrically branched polymer-bioactive material conjugates can be utilized, for example, for the construction of direct sandwich, indirect sandwich, sequential, and competition biological assays.

In yet another aspect of the invention, at least one non-modified and/or modified asymmetrically branched polymer can be utilized to carry at least one protein molecule to various solid surfaces, generating virtually no denaturation of the at least one protein molecule. These surfaces can include nitrocellulose, paper, other membranes, glasses, metals, plastics and the like, can be presented in a variety of forms, such as flat surfaces, such as sheets, strips and so on, spheres, such as particles and beads, and other forms, and can be used, for example, for the generation of plate microarrays based on spatial arrangements for the production of bead, micro or nanoarrays and assays. The bead micro/nanoarrays can either be constructed through the attachment of multiple proteins on the same micro/nanoparticle or by simply mixing the beads, wherein each bead carries one specific kind of a protein molecule. In addition to detection, the bead micro/nanoarrays can also be utilized for rapid, large-scale, high throughput separation of bioactive materials prior to analysis with protein plate microarrays, 2D gels, or mass spectrometers. Such protein arrays are ideal tools for protein target discovery, validation, drug lead screening, as well as monitoring biomarkers and protein profiles during therapeutic treatment.

The asymmetrically branched polymer conjugates may be further used in applications related to agriculture, food safety assurance, as well as in vitro and in vivo diagnostics, therapeutics delivery and targeting. Thus, the polymer conjugates can be used as drug delivery devices, which can provide bolus delivery, delayed released, timed release, enteric coating and various other pharmacological formulations of desired characteristics. Such conjugates may also be utilized as key sensing components in various sensor platforms including, but not limited to, optical, electrical, piezoelectric devices, as well as microfluidics and microelectromechanical systems (MEMS) and nanoelectromechanical systems (NEMS).

BRIEF DESCRIPTION OF THE DRAWINGS

The following description of the figures and the respective drawings are non-limiting examples that depict various embodiments that exemplify the present invention.

FIG. 5 illustrates lateral flow-based immunoassay configurations.

FIG. 7 depicts a comparison of indirect assays constructed with or without random asymmetrically branched polymers. A much higher sensitivity was achieved with ABP-based assays.

DETAILED DESCRIPTION OF THE PRESENT INVENTION

Figure 1:
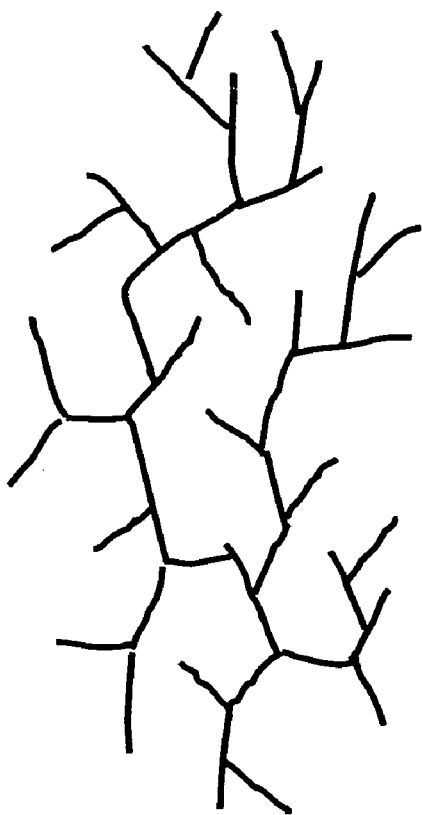
FIG. 1 depicts random (A) and regular (B) asymmetrically branched polymers with asymmetrical branch junctures and patterns.
Figure 1:
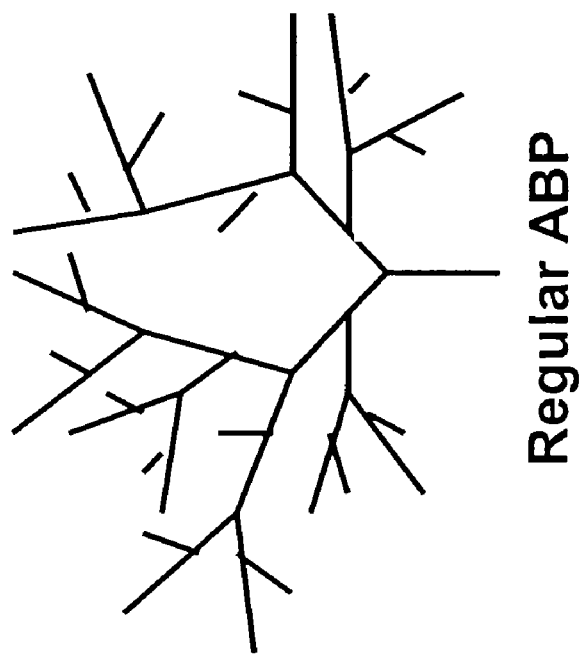

Asymmetrically branched polymers are depicted in FIG. 1, with asymmetric branches, wherein some of the polymers of interest possess no core and exhibit asymmetrical branch junctures consisting of both chain and terminal branches throughout the entire polymer. The functional groups are present both at the exterior and in the interior.

Figure 2:
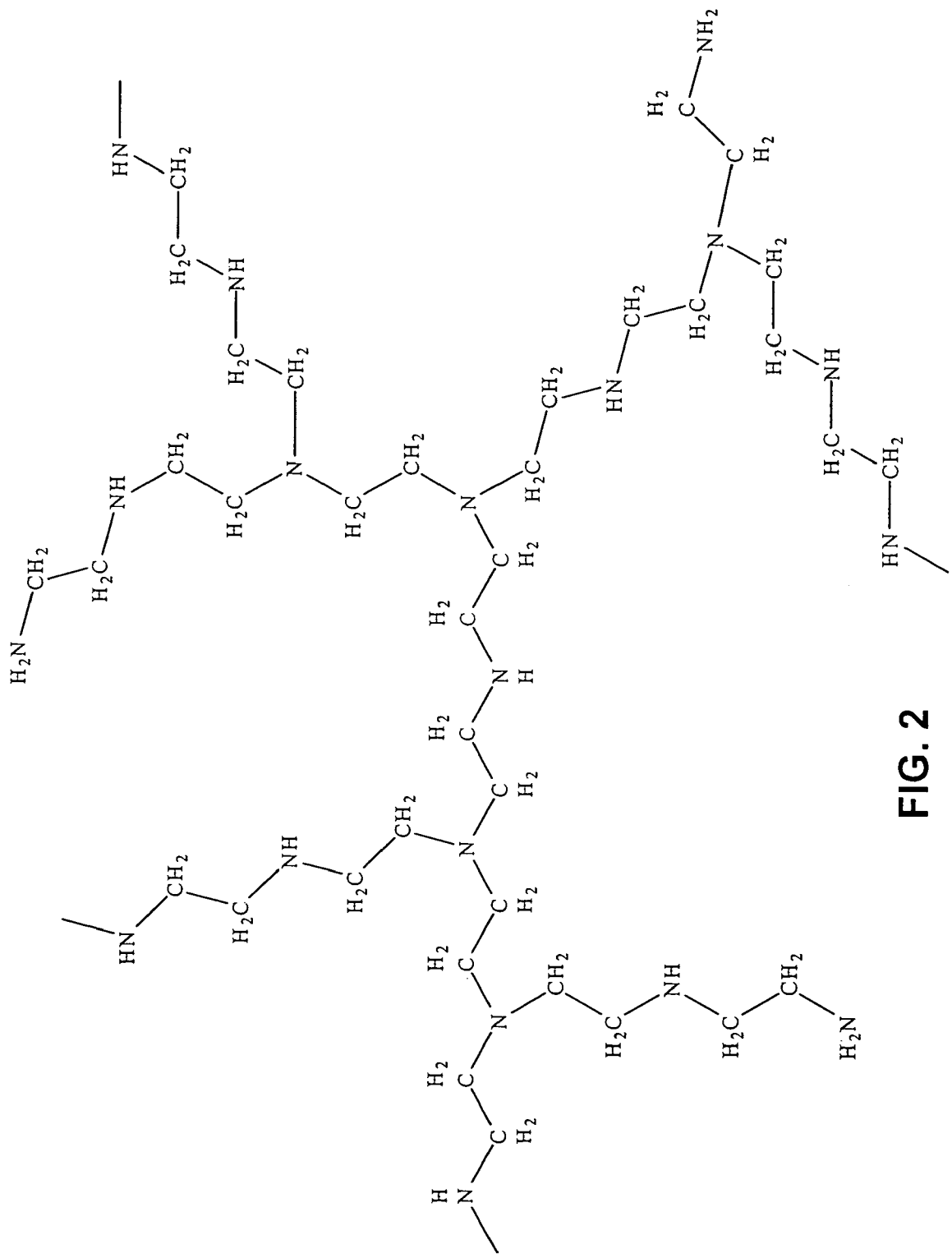
FIG. 2 depicts the chemical structure of a random asymmetrically branched polyethyleneimine polymer.

Such polymers exhibit a number of unique advantages. First, a variety of known starting materials can be employed. Such monomers and polymers are low-cost and very easy to manufacture in large quantities. For example, one such precursor polymer that can be used to synthesize a polymer of interest is polyethyleneimine (PEI). The synthesis of random asymmetrically branched polyethyleneimines was discovered more than six decades ago (G D Jones et al., J. Org. Chem. 9, 125 (1944)) and the synthetic procedures for these precursor polymers are well established. Polyethyleneimines with various molecular weights are commercially available from different sources such as Aldrich, Polysciences, and BASF (under the trade name Luposal™). The random asymmetrically branched polyethyleneimines are primarily produced through cationic ring-opening polymerization of ring-strained cyclic imine monomers, such as aziridines (ethyleneimine) and azetidines (propyleneimine), with Lewis or Bronsted acids as initiators. (O C Dermer et al., "Ethylenediamine and Other Aziridines", Academic Press, New York, (1969), and A S Pell, J. Chem. Soc. 71 (1959)). Since it is a one-pot process, large quantities of random asymmetrically branched polymers can be readily produced. (FIG. 2).

The randomly branched poly(2-substituted oxazoline) polymers can be prepared according to procedures described by M Litt (J. Macromol. Sci. Chem. A9(5), pp. 703-727 (1975)).

Second, the prior art synthetic processes often generate various branch junctures within the macromolecule. In other words, a mixture of terminal and chain branch junctures is distributed throughout the entire molecular structure. The branching densities of these random asymmetrically branched polymers are lower, and the molecular structure is more open when compared with dendrimers and dendrigrafts. Although the branch pattern is random, the average ratio of primary, secondary, and tertiary amine groups is relatively consistent, with a ratio of about 1:2:1, as described by C R Dick et al., J. Macromol. Sci. Chem., A4 (6), 1301-1314 (1970) and G M Lukovkin, Eur. Polym. J. 9, 559 (1973).

Figure 3:
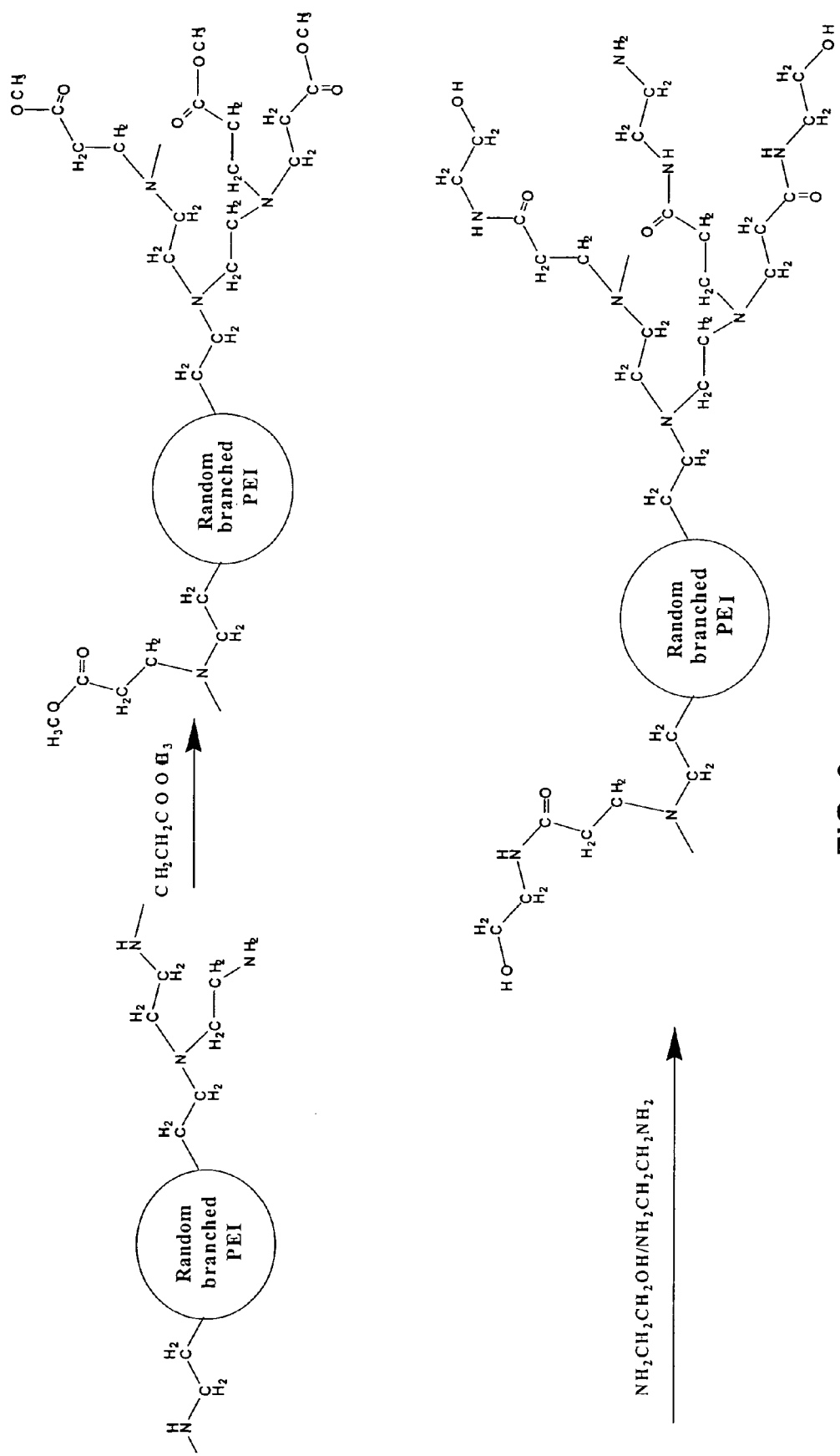
FIG. 3 depicts chemical modification reactions of random asymmetrically branched polyethyleneimine polymers.

Due to the presence of these branch junctures, the random asymmetrically branched polyethyleneimines are still considered spherical macromolecules. Within the globular structure, there are various sizes of pockets formed from the imperfect branch junctures at the interior of the macromolecule. Unlike dendrimers and dendrigrafts where interior pockets are always located around the center core of the molecule, the pockets of random asymmetrically branched polymers are spread unevenly throughout the entire molecule. As a result, random asymmetrically branched polymers possess both exterior and unevenly distributed interior functional groups that can be further reacted with a variety of molecules, thus forming new macromolecular architectures, defined as modified random asymmetrically branched polymers (FIG. 3).

Although having a core, the functional groups of the regular asymmetrically branched polymer are also distributed both at the exterior and in the interior, which is very similar to the random ABP. Again, a variety of precursor polymers can be used to construct such polymers of interest. One such precursor polymer is polylysine. The best example of making such polymers is regular asymmetrically branched polylysine polymers as described in U.S. Pat. Nos. 4,289,872; 4,360,646; and 4,410,688. As a result, such polymers can also be modified in a similar manner as for the random ABPs.

In one embodiment of this invention, the asymmetrically branched polymer (for example, either a random asymmetrically branched polyethyleneimine (PEI) or a regular asymmetrically branched polylysine) was modified with different kinds of primary amine groups through, for example, Michael addition or an addition of acrylic esters onto amines of the polymer. Thus, for example, through a Michael addition reaction, methyl acrylate can be introduced onto the primary and/or secondary amino groups of polyethyleneimine and polylysine polymers. The ester groups then can be further derivitized, for example, by an amidation reaction. Thus, for example, such an amidation reaction with, for example, ethylenediamine, can yield the addition of an amino group at the terminus of the newly formed branch. Other modifications to the polymer can be made using known chemistries, for example, as provided in "Poly(amines) and Poly (ammonium salts)" in Handbook of Polymer Synthesis (Part A) Edited by H R Kricheldorf, New York, Marcel Dekker, 1994.

On such addition, a modified asymmetrically branched polymer, such as, a modified PEI or polylysine polymer, is formed. As an extension of the asymmetrically branched polymer, such as PEI and polylysine, the resulting modified ABP is also asymmetrically branched. Depending on the solvent environment (i.e. pH or polarity), the surface functional groups can carry different charges and charge densities. The molecular shape and functional group locations (i.e., functional group back folding) can then be further tuned, based on these characteristic properties.

In another embodiment of this invention, the modified asymmetrically branched polymers can be produced using any of a variety of synthetic schemes that, for example, are known to be amenable to reaction with a suitable site on the polymer. Moreover, any of a variety of reagents can be used in a synthetic scheme of choice to yield any of a variety of modifications, or additions to the polymer backbone. Thus, for example, in the case of the Michael addition reaction to an amine described above, the addition of any of a variety of monomers can be used at the alkylation stage with a $C_1$-$C_{22}$ acrylate. Preferred reactants, include methyl, ethyl, propyl, butyl, pentyl, hexyl, heptyl, octyl, nonyl, decyl, undecyl, dodecyl acrylate and mixtures thereof. Similarly, at the amidation stage in the example exemplified above, any of a variety of amines can be used. For example, ethylenediamine, monoethanolamine, tris(hydroxymethyl)aminomethane, alkyl amine, allyl amine, or any amino modified polymers including polyethylene glycol (PEG), perfluoropolymers, polystyrene, polyethylene, polydimethylsilixane, polyacrylate, polymethylmethacrylate, and the like, and mixtures thereof, can be used.

This synthetic strategy would allow not only asymmetric growth of the molecule, where more pockets can be readily introduced, but also the addition of multiple functional groups at both the interior and the exterior of the structure. Obviously, one can continuously modify the precursor polymer using the same or a different synthetic process until the desired asymmetrically branched polymers with appropriate molecular weights and functional groups are attained. In addition, the hydrophobic and hydrophilic properties, as well as charge densities of such polymers, can be readily tailored to fit specific application needs using appropriate monomers for constructing the polymer, and suitable modification reactions.

In another embodiment of the invention, the chain end of random asymmetrically branched polyoxazoline can be terminated or reacted with another small molecule to generate various functional groups at the polymeric chain ends including primary, secondary or tertiary amines and carboxylate, hydroxyl, alkyl, fluoroalkyl, aryl, PEG, acetate, amide, and/or ester groups. Alternatively, various initiators can also be utilized so that the same type of functional groups can be introduced at the chain end (J. Macromol. Sci. Chem. A9(5), pp. 703-727 (1975)). Therefore, an alkyl modified, random asymmetrically branched poly(2-ethyloxazoline) with primary amine chain ends can be prepared using M Litt's procedure, supra.

In another embodiment of this invention, asymmetrically branched polymers can be utilized to carry bioactive materials for both in vitro and in vivo related applications. The bioactive materials comprise a variety of molecules, particularly those with the ability to bind another molecule, such as a biological polymer, such as a polypeptide, a polynucleotide, a lipid, a polysaccharide, an enzyme, a receptor, an antibody, a vitamin, a lectin and so on. The target may be a pathogen, such as a parasite, a bacterium, a virus, or a toxin, such as venom. The bioactive materials can be used for a variety of uses, including as a diagnostic agent, a therapeutic agent and so on. By "diagnostic agent" is meant a molecule which can be used as a marker for a particular disease, physiological state or stage, a pathological stage or state, and so on. Albumin, mineral level, microorganism, specific antibody, specific antigen, toxin and so on are examples of diagnostic agents. Therapeutic agents are those that confer a beneficial effect, such as a drug, a nutrient, a protein and so on. It is not uncommon for a particular target to be both a diagnostic agent and a therapeutic agent.

Due to the ability to produce unevenly distributed pocket sizes and various functional groups either in the interior or at the exterior, these asymmetrically branched polymers, on proper modification, are capable of carrying a variety of materials ranging from small molecules, such as metal ions and drugs, to other large bioactive materials, such as proteins and DNA.

A polymer of interest may be used to encapsulate a bioactive molecule, particularly pharmaceuticals.

The microcapsule can be made as taught herein and as known in the art, see, for example, Microencapsulation, Methods and Industrial Applications, Benita, ed., Dekker, 1996. The microcapsules can be made in a dry state mixture or reaction, or can be made in a liquid state mixture or reaction.

Microcapsules can be administered to a host in a variety of ways including oral, IM, SC, IV, rectal, topical and so on, as known in the art.

The instant microcapsules can be used in topical applications, such as creams, ointments, lotions, unguents, other cosmetics and the like. Pharmaceuticals and other bioactive or inert compounds can be encapsulated such as emollients, bleaching agents, antiperspirants, pharmaceuticals, moisturizers, scents, colorants, pigments, dyes, antioxidants, oils, fatty acids, lipids, inorganic salts, organic molecules, opacifiers, vitamins, pharmaceuticals, keratolytic agents, UV blocking agents, tanning accelerators, depigmenting agents, deodorants, perfumes, insect repellants and the like.

Metals that can be carried by a polymer of interest may include, but are not limited to, transition metals and others, such as Sc, Y, Ti, Zr, Hf, V, Nb, Ta, Cr, Mo, W, Mn, Tc, Re, Fe, Ru, Os, Co, Rh, Ir, Ni, Pd, Pt, Cu, Ag, Au, Zn, Cd and Hg, alkali metals, alkaline-earth metals, Lanthanide series elements, such as Ce, Pr, Nd, Pm, Sm, Eu, Gd, Tb, Dy, Ho, Er, Tm, Yb and Lu, and Actinide series elements, such as Th, Pa, U, Np, Pu, Am, Cm, Bk, Cf, Es, Fm, Md, No, and Lr.

Drugs that can be carried by a polymer of interest include, but are not limited to, anesthetics, antibiotics, antifungals, antivirals, analgesics, antihypertensives, antiinflammatories, antidotes, antihistamines, chemotherapeutic agents, hormones, antidepressants, depressants, stimulants, tranquilizers, urinary antiinfectives, vasoconstrictors, vitamins, cardioactive drugs, immunosuppressives, nutritional supplements, and the like. Specific examples are lidocaine, bupivacaine, hydrocortisone, chlorpheniramine, triprolidine, dextromethorphan, codeine, methidizine, trimeprizine, atropine, 2-PAM chloride, homatropine, levodopa, cyclizine, meclizine, scopolamine, acetaminophen, amphotericin B, amphetamine, methamphetamine, dextroamphetamine, propanolol, procainamide, disopyraminide, quinidine, encainide, milrinone, amrinone, dobutamine, enalapril, colnidine, hydralazine, guanadrel, ciprofloxacin, norfloxacin, tetracycline, erythromycin and quinolone drugs.

Large bioactive materials that can be carried by a polymer of interest may include, but are not limited to, proteins, recombinant proteins, antibodies, $F_{ab}$ antibody fragments, other antibody fragments that bind antigen, enzymes, DNA, recombinant DNA, DNA fragments, RNA, RNAi, recombinant RNA, RNA fragments, nucleotides, viruses, virus fragments and so on.

In yet another embodiment of this invention, these asymmetrically branched polymers can be used to manipulate biological sensing events at the nanometer scale. The preferred conjugates of the present invention include those where asymmetrically branched polymer conjugates comprise at least one asymmetrically branched polymer associated with at least one unit of at least one biologically active material or biological response indicator.

The biologically active material, biological response indicator or therapeutic molecule often is one that has a recognition or binding ability. For the purposes of the instant invention, those molecules of interest that have a recognition or binding ability will be identified as binding pairs, or individually as one of or one member of a binding pair. Thus, examples of binding pairs include, antibody and antigen; antigen-binding portion of an antibody and antigen; the $F_c$ portion of an antibody and an $F_c$ receptor; avidin, streptavidin, neutral avidin, NeutraLite avidin or other avidin derivatives and analogs and biotin; hormone receptor and hormone; nucleic acid binding moiety, such as a protein and a target nucleic acid, such as a restriction enzyme; enzyme and substrate; enzyme and cofactor; one strand of a nucleic acid and the complementary strand of nucleic acid; enzyme and nucleic acid recognition site, as with restriction enzymes; lectin and the cognate saccharide; and so on. Any set of molecules that exhibit a specific binding reaction where the binding therebetween can be exploited for detecting presence or one or the other can be used in the practice of the instant invention.

Some examples of these biologically active materials are interleukins, interferons, T-helper cell CD4 molecule, $F_c$ receptor, acetylcholine receptor (AChR), T cell receptor for antigen, insulin receptor, tumor necrosis factor, granulocyte colony stimulating factor, hormone receptor, antibodies, antibody fragments, IgG molecules, $F_{ab}$ antibody fragment molecules, recombinant proteins, polypeptides, phage, phage fragments, DNA fragments, RNA fragments, hormones, such as, insulin and hCG, enzymes, sialic acid, porphyrins, nucleotides, viruses, viral fragments and the like.

In general, the ligand molecules include antigens (i.e. bacteria, viruses and toxins), antibodies (i.e. IgG and IgE molecules), antibody fragments, $F_{ab}$ fragments, polypeptides, hormones (i.e. insulin and hCG), neurotransmitters (i.e. acetylcholine), DNA fragments, RNA fragments, enzymes (i.e. organophosphate acid anhydrolase (OPAA) and organophosphate hydrolase (OPH)), small molecules, such as sialic acid, porphyrins and nucleotides, or other receptor molecules well know to those of ordinary skill of art. Preferred ligands in this invention are IgG, $F_{ab}$, and other antigen binding portions of immunoglobulins, whether derived from naturally occurring immunoglobulin or protein made recombinantly.

Receptors are biomolecules (i.e. proteins or polysaccharides) often present at the cell surface, and often partially embedded in or traversing the cell plasma membrane. The receptors are capable of recognizing viruses, antigens, neurotransmitters, hormones and the like. For example, T helper cell CD4 molecule is a virus-specific receptor of HIV, while T cell receptor recognizes specific antigens. Acetylcholine receptor (AChR) binds the neurotransmitter, acetylcholine, whereas hormone receptors such as the adrenergic or insulin receptor recognizes adrenaline and insulin, respectively. Others may include $F_c$ receptors on macrophages, which is a receptor of immunoglobulin. These receptors or receptor moieties can be isolated from the biological systems, or synthesized through either biotic or abiotic routes. Therefore, these newly developed receptor molecules or moieties can also be utilized as ligands for nanomanipulation applications.

While the above assay formats are exemplified by the use of antibodies and fragments thereof arising from the antigen binding activity thereof, the polymers of interest can be used with other molecules with antigen-binding ability. Examples of such other molecules include nucleic acids, such as, deoxyribonucleic acid and ribonucleic acid, and receptors, such as hormone receptors isolated from cells or produced recombinantly.

The joining of a polymer of interest with another molecule of interest, such as a bioactive molecule, such as a protein, such as an antibody or antigen, a nucleic acid, biotin, streptavidin, colloidal gold and the like, is carried out using known methods, such as, chemical synthetic methods using the chemical characteristics of the polymer or modified polymer and of the molecule to be bound thereto. Thus, the polymer can be modified to contain, for example, amine groups that can be used as the reactive site to which a molecule of interest can be bound through covalent linkages. Alternatively, the joining may occur by mere mixing of the polymer and molecule to be bound through non-covalent linkages therebetween. The linking of another entity to the polymer of interest can also be achieved through a combination of both. For example, a polymer of interest can be covalently linked to a ligand, followed by physical adsorption of a reporter particle through non-covalent linkages to form a ligand-polymer-reporter particle conjugate, which can be readily used for bioassays.

When preparing protein-based assays or detection systems based on these immunoassay formats, one often encounters three major difficulties: denaturation, adhesion/immobilization and orientation of proteins. A protein or antibody molecule often folds into a three-dimensional structure in solution to maintain biological activity. On interaction with different solid surfaces, for example, during immobilization onto membranes, glass slides, or micro/nanoparticles, the three-dimensional structure of the protein molecule often collapses, thus losing biological activity.

Also, some proteins are simply not amenable to fixation onto a solid phase. To affix certain proteins onto a solid phase often requires chemical reaction or electrostatic interaction intervention. However, such reactions may impact the secondary and tertiary structures of a biomolecule of interest, as discussed hereinabove. Moreover, heterogeneous chemical reactions often may not run to completion or inherently do not have reaction kinetics highly in favor of the desired product. That can yield a mixture including unwanted reactants and side products.

In some cases, the reactions can inadvertently denature, partially or completely, the protein to be bound to a solid surface.

Electrostatic reactions rely on isoelectric points and dipole moments of the proteins of interest. Moreover, those characteristics are dependent on the environment of the protein, for example, on the pH and composition of the buffer.

Thus, those approaches can and often lead to undesirable results, such as poor yield of the desired product, and reproducibility in general. From the standpoint of commerciability, the result is poor lot-to-lot consistency.

Therefore, the physical deposition strategy, although low in cost, gives a completely random orientation of the binding ligands. On the other hand, the multistep chemical attachment approach provides improved orientation. However, the latter is often too expensive, and also tends to give irreproducible results due to incomplete chemical reactions.

The polymers of interest can be used to advantage in bioassays. A variety of assay formats exist and any are amenable to improvement using a polymer of interest. Examples of such known assay formats are provided hereinbelow.

An antibody based "sandwich" assay consists of three components: a capture antibody, an antigen and a detector antibody linked with a reporter (i.e., an enzyme, a fluorophore, a colored particle, a dyed particle or a particle containing a dye, a stained particle, a radioactive label, quantum dots, nanocrystals, up-converting phosphorescent particles, fluorophore or dye-containing polymer or latex beads that are detectable visually and/or with mechanical assistance and so on). Such an assay often requires three separate experimental steps. The first step involves immobilization of the capture antibody on a solid surface, followed by a subsequent addition of an antigen solution to form an antibody-antigen complex. The last step is to add a reporter group comprising a labeled detector antibody to generate a capture antibody-antigen-detector antibody complex. As a result of this "sandwich" assay, the unknown antigen can be identified, as well as the quantity and concentration of the antigen, which can be quantified, for example, with an optical reader. If the antigen is not present in the sample solution, no "sandwich" complex will be formed, and thus no signal will be observed.

The actual structure of "sandwich" complexes is highly dependent on the binding reagents and reporter moieties. The various assay formats can be exemplified using colloidal gold as the reporter molecule. It is well known in the art that the formation of capture antibody-antigen-detector antibody-gold particle complexes results in a positive test. However, in reality, during the synthesis of gold-labeled detector antibody, it was found that the antibody often is randomly oriented on the gold surface due to variations in dipole moment and isoelectric point of different proteins, for example. As a result, a precrosslinked product, which consisted only of detector-gold antibody aggregates, was formed, even without the presence of antigen. This precrosslinked product raised the noise or background level very significantly, and in some cases, generated very serious false positive readings.

The asymmetrically branched polymer based assays, on the other hand, generate a clean, but very different immunocomplex: capture antibody-antigen-detector antibody-ABP-particle. In this case, only a clean immunocomplex is formed, and the precrosslinked products are completely eliminated. As a result, the assay sensitivity is significantly enhanced, and false positive readings are dramatically reduced. In addition, much smaller amounts of reagents are utilized when compared with standard antibody-based assays that do not employ the polymers of interest. Moreover, the capture antibodies can also be attached onto different solid surfaces through ABP using a similar immobilization strategy. This approach is independent of dipole moment and isoelectric point of proteins, thus greatly simplifying assay construction processes and all the while maintaining the protein of interest in native configuration or at the least, in a configuration that maintains particular binding sites and epitopes of interest.

The second assay configuration is based on a sequential assay format for the detection of antibodies in unknown samples. In this case, an antigen or fragment thereof carrying an epitope is applied to the solid surface. During the test, the antigen will bind with the targeted antibody, which subsequently reacts with another generic anti-species antibody labeled with colloidal gold. Therefore, the characteristic red color indicates a positive test, while no color change indicates a negative test. A polymer of interest can be used to affix the antigen to the solid phase, as well as used to label an antibody of interest as described hereinabove.

The third assay configuration is an indirect sandwich assay format. In this case, a capture antibody is applied to the membrane surface. During the test, the capture antibody will bind with the targeted antigen, previously linked with an intermediate linker molecule, for example, a biotin or a fluorescein, which subsequently reacts with streptavidin or anti-fluorescein antibody labeled with colloidal gold. Therefore, the red color indicates a positive test, while no color change indicates a negative test. Again, a polymer of interest is used to attach proteins of interest to a solid phase and to mediate the labeling of proteins with a label, such as an additional reactant, such as the biotin or streptavidin, and the like.

In addition, one or multiple biotin or fluorescein-linked enzyme molecules, such as HRP, can also be attached to streptavidin or an antifluorescein antibody-labeled colloidal gold particle. On addition of substrate molecules, the signal can be further enhanced because of the multiple reporter molecules.

Alternatively, the capture antibody can bind a complex which consists of antigen-detector antibody previously linked with an intermediate linker molecule, for example, a biotin or a fluorescein, followed by reaction with streptavidin or anti-fluorescein antibody labeled with colloidal gold. A red color again indicates a positive test, while no color change indicates a negative test.

Another aspect of this invention is to link detector antibody to the colloidal gold particles through biotin-streptavidin-ABP or fluorescein-anti-fluorescein-ABP linkages. This will allow the rapid construction of various sandwich-based assays and microarrays.

Another aspect of this invention is to first label an antigen or a mixture of antigens with an intermediate linker such as biotin or fluorescein. The capture antibody can bind the reporter molecule on the antigen, such as biotin/fluorescein that is conjugated to an antigen, or an epitope of the antigen followed by detecting bound antigen with streptavidin or antifluorescein-labeled reporters, for example. The negative test shows no color changes, while the positive test is indicated by a color change. Again, the polymer of interest is utilized to link streptavidin or antifluorescein-antibody to reporters, i.e., colloidal gold particles.

The fourth assay configuration is based on a competition format. The capture antibody is immobilized on a solid phase, and the antigen is labeled with, for example, colloidal gold particles. In the absence of targeted antigen, the gold-labeled antigen will directly react with the capture antibody, thus generating the characteristic red color, which is interpreted as a negative test. In contrast, in the presence of targeted antigen, due to steric effects, the targeted antigen will bind the capture antibody faster and stronger than the gold-labeled antigen, thus generating no color change, which is interpreted as a positive test. Conversely, a reverse antigen/antibody configuration could also be utilized.

Figure 4:
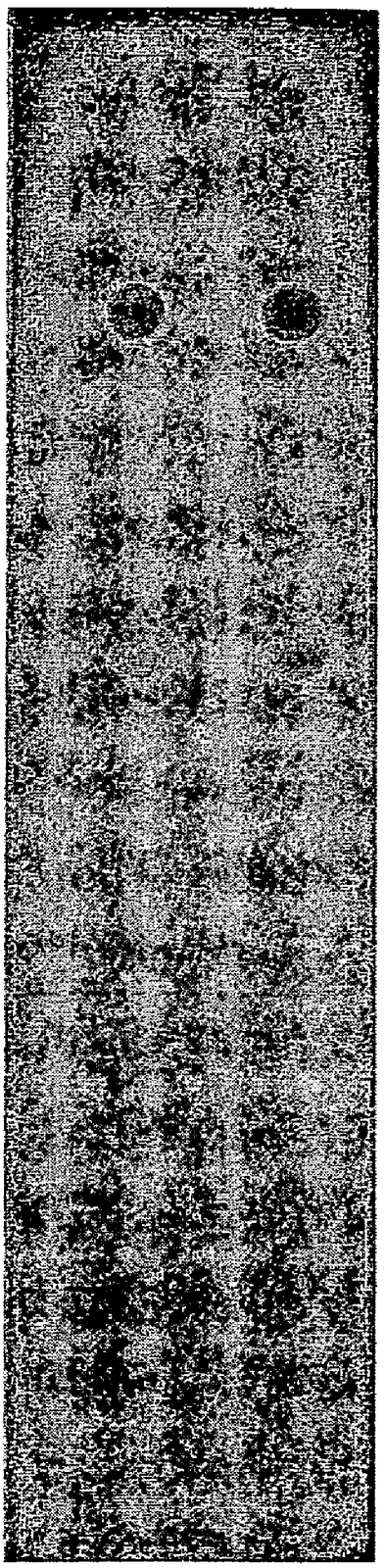
FIG. 4 depicts a protein microarray constructed with asymmetrically branched polymers for the detection and quantification of multiple antigens simultaneously.

The fifth assay configuration is to use any of the above four assay formats, or any other assay format that directly or indirectly detects and/or quantifies a target of interest to construct protein microarrays for the detection and quantification of multiple antigens using, for example, an optical reader for quantification (FIG. 4).

Any of a variety of assay formats can be used in the practice of the instant invention. The artisan can well configure an assay using reagents that will be amenable to identifying a target compound of interest.

The instant assay can be configured as a qualitative assay, such as the commercially available pregnancy assay kits that yield a "yes/no" visible reaction. The instant assay also can yield quantitative results by providing graded amounts of reactants, suitable controls and a set of control reactions using known reagents to provide a "standard curve" to serve as a reference. Configuring an assay to provide quantitative results is known in the art with guidance obtainable in any of a variety of texts and publications.

Figure 5A:
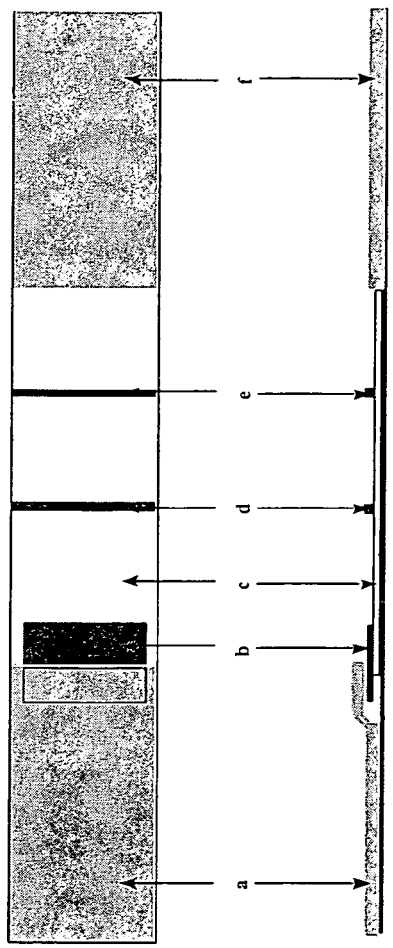
FIG. 5A. Configuration of an immunoassay ticket without a plastic cover: (a) adsorbent pad, (b) conjugate release pad, (c) membrane, (d) zone containing capture antibody, (e) zone containing control antibody, and (f) receiving pad.
Figure 5B:
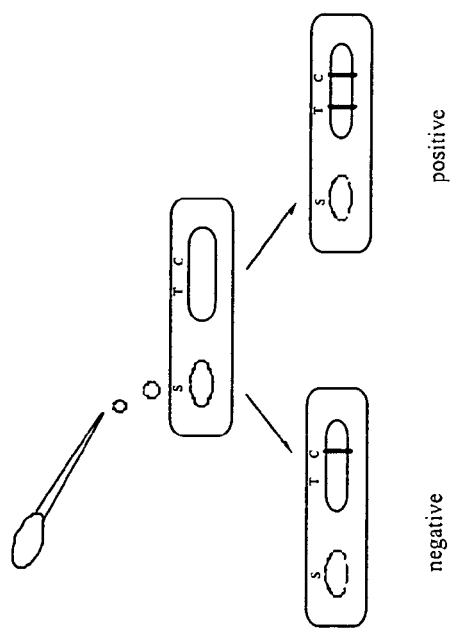
FIG. 5B. An illustration of positive and negative immunoassay tickets in a lateral flow assay format on addition of sample solutions. The dipstick assays worked in a similar manner. (S) sample well, (T) test line and (C) control line.

In one aspect of this invention, the asymmetrically branched polymer is covalently linked with a bioactive molecule (i.e. an IgG antibody, avidin, or streptavidin). The resulting conjugate is allowed to react with colloidal gold particles. The resulting antibody-ABP-gold conjugate can be incorporated into a lateral flow immunoassay as depicted in FIGS. 5A and 5B.

The asymmetrically branched polymer provides three unique features. First, the asymmetrically branched polymer serves as a spacer molecule between the antibody and the solid surface or particle surface. Second, the asymmetrically branched polymer acts as a carrier to transport the bioactive molecules, as well as acting as an anchor to adhere these molecules onto a solid surface from a solution with only the asymmetrically branched polymer portion of the conjugate touching the surface. Third, during this anchoring process, the asymmetrically branched polymer-bioactive molecule conjugate also self-orients the complex at the solid surface.

Figure 6:
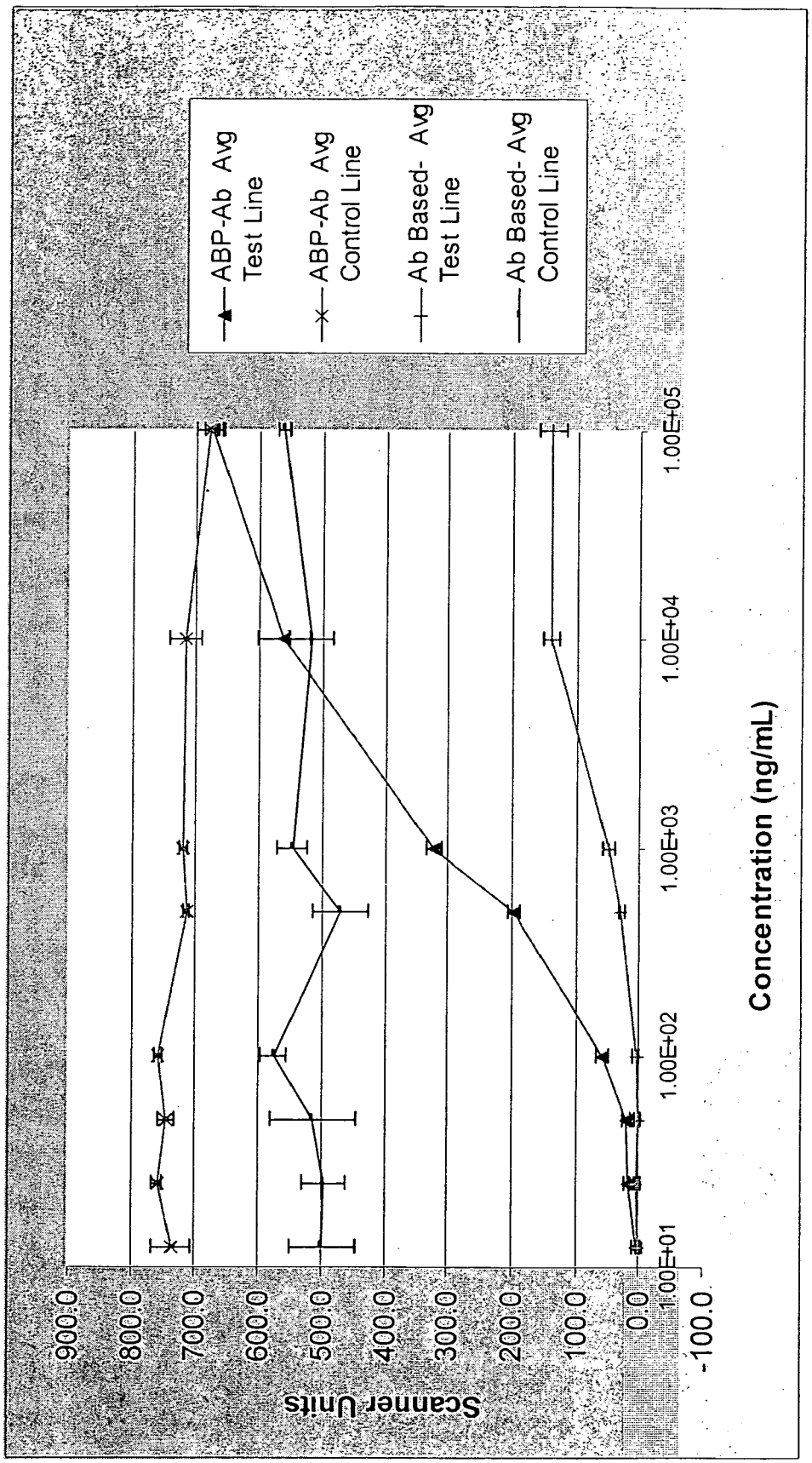
FIG. 6 depicts a comparison of assay performance of modified random asymmetrically branched PEI polymer-antibody-based assays with antibody-based lateral flow tests for the detection of ricin toxoid.

FIG. 6 depicts the assay performance comparison results of a modified random asymmetrically branched PEI polymer-antibody conjugate using a lateral flow assay format. As explained earlier, when antibody is directly adsorbed onto a solid surface (i.e. colloidal gold surface), the antibody molecule tends to lose activity very rapidly due to denaturation. In addition, the linkage between antibody and colloidal gold generally heavily depends on the isoelectric point of the antibody. In most cases, the electrostatic interaction between antibodies and gold particles is not strong enough, thus producing a variety of undesired side products resulting from dissociation, which often causes serious false positive reactions and stability problems. Therefore, the asymmetrically branched polymer-antibody conjugates provide much better assay results in terms of sensitivity, stability, and reproducibility.

As shown in FIG. 6, the quantitative assay results as indicated by optical density measurements (scanner units) demonstrates a positive correlation of signal increase with an increase of antigen (ricin toxoid) concentration. A very dramatic sensitivity difference was observed when comparing modified ABP-anti ricin conjugate-based assays with just antibody-based test strips. If 30 scanner units (an untrained individual can easily identify the test lines) are set as a minimum for a positive test, the ABP-based assay is at least 60-fold more sensitive than the corresponding antibody-based assays. At higher concentrations, the results were even more dramatic, with optical densities rapidly increasing with increasing concentrations in the ABP-Ab-based assays, while the Ab-based assay test line eventually formed a plateau despite an increase in concentration.

The data again proved that without the utilization of an ABP, a majority of antibody molecules were either denatured or poorly oriented at the solid phase surface. The ABP served not only as a carrier, but more importantly as an anchoring spacer for the antibody molecules when immobilized from a solution onto a solid surface, thus completely eliminating the protein denaturation problem. The drastic differences in optical density responses over various concentrations also provided a quantitative method for the determination of unknown sample concentration. In contrast, in the same concentration range, the antibody-based assays are much less responsive over concentration changes, and thus are not as suitable for quantitative measurements.

In addition to the significant enhancement in sensitivities, the ABP-Ab-based lateral flow assays are also more amenable for medical diagnostics, target discovery, as well as monitoring biomarker changes and protein profiles during clinical trials and therapeutic treatments.

The "indirect" sandwich assay was also constructed in a microarray format for the detection of botulinum toxoid. As shown in FIG. 7, when ABP was used to attach streptavidin to colloidal gold, the intensity of the reaction was dramatically improved when compared with the non-ABP assays, thus greatly increasing the assay sensitivity. The result is to enhance a positive signal. Using the same principle, assays and microarrays based on sandwich, competition, or sequential assay formats can be readily produced.

The conjugates of interest comprising one of a binding pair, a random asymmetric branched polymer of interest and a reporter molecule can be configured into a number of different assay formats, wherein one, two, three, four or more targets can be monitored simultaneously. Such simultaneous assays can be conducted using one or more devices that carry the conjugates on a suitable solid phase, as described herein and as known in the art, such as plastic, such as a microtiter plate, or a membrane, such as nitrocellulose. A single device can contain a plurality of conjugates to detect a plurality of targets. Such a multiplex device can detect two, three, four or more targets.

The ABP-Ab conjugates once attached onto colloidal gold nanoparticles (5-100 nm) or latex beads (0.2-1 µm) can also be utilized to produce bead-based nanoarrays or microarrays. In either case, either one antibody per bead or multiple antibodies per bead can be synthesized. The bead nano/microarray was found to be very effective for separating and detecting targeted proteins from biological fluids such as serum, plasma, whole blood, saliva, and urine.

Once the above assay configuration is incorporated, it can be seen that the number of molecules or markers detected can be single or plural in an assay or on a device. Thus, a chip microarray can also be constructed (FIG. 4). Using the same principle, a high-density microarray can also be developed for the simultaneous identification of multiple targets including proteins, toxins, viruses, bacteria, bacterial spores, drugs, chemical agents, pollutants and/or any other target of interest. The resulting microarrays can be constructed using a lateral flow assay format. Another assay format is a bead array, as offered by BD Illumina and Luminex, a plate microarray, a bead microarray or a combination thereof.

Such assays can be configured to contain a plurality of biomarkers that are diagnostic for a desired purpose. Thus, such a multiplex device, which can be a nanoarray or microarray, can be diagnostic for a pathologic state, reveal reaction to stimulus, such as a food or drug, and so on. The number of biomarkers used will depend on the endpoint and generally will be the minimal number of markers needed to demonstrate whether the endpoint exists. Thus, as known in the art, determining exposure of a host to a pathogen can rely on a single diagnostic antibody that binds said pathogen. Reactivity to a drug may require a larger number of biomarkers as the impact of a drug on a host may trigger reaction in a number of cellular functions. Moreover, the biomarkers used may need to be optimized to operate on a majority of an randomly breeding population or a plurality of assays may be required using different sets of biomarkers in each assay.

The preferred conjugates of the present invention include those where an asymmetrically branched polymer conjugate comprises at least one asymmetrically branched polymer associated with at least one unit of at least one biologically active material or biological response indicator. The polymer of interest can include those that do not contain a core or those that contain a core, such as those disclosed in the Denkewalter et al. patents. The preferred asymmetrically branched polymer of the present invention includes those where an asymmetrically branched polymer comprises at least one random or regular asymmetrically branched polymer constructed by at least one type of monomer capable of forming additional branches. As described herein, some of the polymers of interest do not contain a core. Some examples of random and regular asymmetrically branched polymers are randomly branched polyethyleneimines, polypropyleneimines, polyamidoamines, and regularly branched polylysine.

The surfaces to which the asymmetrically branched polymer conjugate may be bound are varied and may include glass, nitrocellulose, paper, quartz, plastic, metal, colloidal particles including colloidal gold, colloidal silver and colloidal platinum, polymer or latex beads, inorganic particles, silicon wafers, colored latex particles, particles containing fluorescent or colored materials, clay, ceramic, silicon-based or ceramic semiconductor particles, silicon or ceramic semiconductor chips, nanocrystals, quantum dots, and up-converting phosphorescent particles. Quantum dots are inorganic nanoparticles (often less than 5 nm in diameter) capable of emitting different colors of light by controlling the composition and size of the material contained within the particle. Up-converting phosphors are submicron ceramic microparticles that emit visible light on excitation with near-infrared light. Such particles have sizes ranging from 100 nm to 500 nm and comprise rare earth ions, e.g., ytterbium, which are capable of absorbing two photons of infrared light. Due to the absence of autofluorescence in the background, these microparticles are often utilized as a tagging moiety for biological assays.

The assays comprising asymmetrically branched polymers of interest and a moiety with drug binding ability can be used to monitor drug presence and levels in a recipient of a drug. Such a moiety can be an antibody, an antigen-binding portion of an antibody or a ligand, for example. The drug to be monitored can be any drug, including those mentioned herein, and further including cox-2 inhibitors, NSAIDs, antimitotics, antibiotics, antivirals, and the like, for example, warfarin, phenytoin, digoxin, carbamazepine, methotrexate, phenobarbital, procainamide, valproates, theophylline, cyclosporin, tacrolimus, gentamycin, tobramycin, amikacin and vancomycin.

The instant invention contemplates kits comprising storable, shelf-stable reagents that comprise an assay, such as those described hereinabove. Shelf stability can be gauged by storage time at room temperature, at refrigerator temperatures and so. The kits can comprise a plurality of vials comprising liquid reagents or desiccated reagents to be reconstituted with an appropriate diluent, such as sterile water or a buffer. The kit can comprise a device housing the various reagents, such as a known pregnancy test kit, a lateral flow immunoassay kit and so on. Thus, the assay format for the kit can be in the form or shape of a dipstick, a wand, a slide and the like. Generally such devices comprise a plastic holder with appropriate solid phases, such as a plastic, a membrane, a paper and the like.

The results of the assays of the instant invention can be ascertained in a qualitative manner, such as in a dipstick assay with a visual readout. Such assays are known and exemplified by various immunoassays, such as pregnancy test kits and the like.

The results of the assays of the instant invention can be ascertained by a mechanical means. The mechanical means can be any physical device that senses or detects the particular physical characteristics of the reporter molecule or a product of the reporter molecule. The mechanical device can be one that is situated in a laboratory setting, or may be situated in a movable setting for point of use applications, such as a hand held device. The device can be made into smaller, portable formats for more directed point of use applications, such as in a hospital room, physician's office, in the field and the like. Examples of portable devices and hand-held devices that can be used to detect spectrophotometric, luminescent, chemiluminescent, fluorescent or colorimetric reporter molecules are provided, for example, in U.S. Pat. Nos. 5,083,868; H1563; 6,480,115; 6,394,952; 5,900,379; 6,663,833; 6,656,745; 6,267,722; 6,706,539; 5,646,735; 6,346,984; 6,002,488; 5,962,838; 4,917,495; 6,575,368; and 6,583,880.

Such a mechanical device is one that has a detecting or sensing means for ascertaining, particularly the reporter molecule. A detecting means is one that is suitable for determining the presence of a particular reporter molecule. A radioactive reporter molecule is detectable with, for example, a scintillation counter or a Geiger-Muller counter. A light-emitting, fluorescent or luminescent reporter molecule is detectable with, for example, a colorimeter, a refractometer, a reflectometer, a photosensing device comprising, for example, a photomultiplier tube, a scanner, a charge coupled device (CCD) image sensor, a complementary metal oxide semiconductor (CMOS) image sensor and the like.

The device also can comprise a data processing means whereby the detected signal is processed and digitized. The processing means often is termed a central processing unit, a CPU, or a microprocessor, such as a semiconductor chip where data processing and analysis occurs. The digitized information either is stored in a self-contained data storage device, such as a tape, diskette, hard drive and the like or is communicated via data communication means, such as wired computer communication means or by wireless means using appropriate means, such as infrared, radiowave, microwave and the like, to a remote data storage means or a data processing means wherein the information is analyzed.

The device can contain a data input means. For example, the device can include a keyboard, a scanner and the like to provide commands for implementation by the device or to associate identifying information with data. The scanner can be one that obtains and stores an image, or can be one that interprets a code, such as a bar code, see for example, U.S. Pat. Nos. 5,885,530 and 6,099,469.

Thus, the remote detecting device can contain data processing means, such as a circuit board having an integrated circuit thereon, see for example, U.S. Pat. Nos. 5,494,798 and 6,480,115, with software to control operation of the device. The remote device can comprise a data storage means, which may be removable, such as a diskette, "stick" and other data storage forms. If not removable, the stored data can be accessible via a data communication means. Such communication means can be a hard wire for direct download of data, or such communication can take an alternative form as known in the art, such as wireless signal, for example, shortwave signals, such as radio frequencies, microwaves and infrared. Such wireless signals can be transmitted via antennae or by satellite.

For example, the information can be analyzed to compare experimental and control runs. Alternatively, the experimental run, either as a raw figure or as a figure corrected by the control is compared to population mean values. The data reduction and analyzing can be accomplished using any of a variety of available algorithms or which can be developed to yield software means for obtaining the appropriate analysis of data and to obtain a suitable output of results.

The device can contain a display means, such as a CRT or liquid crystal display, wherein the detected and/or analyzed data is appropriately processed, for example, compared with control data relating to previously obtained population data, and the data is provided to the device operator. The data can be presented as desired, for example as provided hereinabove, the raw data, relative data once adjusted for control values, or both, can be displayed on the remote device, see for example, U.S. Pat. No. 5,885,530 for point of use results.

Alternatively, the digitized information can be communicated to a data storage means, the data storage means being contained within the device or separate from the device. The digitized information can be communicated to the external storage means using known communication means. The data contained in the storage means then can be communicated with a CPU for appropriate data analysis.

Examples of such devices with data processing interfaces and means include U.S. Pat. Nos. 5,543,920; 5,589,932; and 6,362,886.

The conjugates of interest can carry a therapeutic bioactive molecule and can be incorporated into pharmaceutical compositions suitable for administration. For example, the polymers of interest can be used to coat or to encapsulate a bioactive molecule, such as a pharmacologically active molecule, such as a drug, such as insulin. Such compositions typically comprise the active ingredient composition and a pharmaceutically acceptable carrier. As used herein, the language "pharmaceutically acceptable carrier" is intended to include any and all solvents, dispersion media, coatings, antibacterial and antifungal agents, isotonic and absorption delaying agents and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds also can be incorporated into the compositions.

A pharmaceutical composition of the invention for use as disclosed herein is formulated to be compatible with the intended route of administration. Examples of routes of administration include parenteral, e.g., intravenous, intradermal, subcutaneous, oral (e.g., inhalation), transdermal (topical), transmucosal and rectal administration. Solutions or suspensions used for parenteral, intradermal or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates, and agents for the adjustment of tonicity such as sodium chloride or dextrose. The pH can be adjusted with acids or bases, such as HCl or NaOH. The parenteral preparation can be enclosed and stored in ampoules, disposable syringes or multiple dose vials made of glass or plastic.

Pharmaceutical compositions suitable for injectable use include sterile aqueous solutions (where water soluble) or dispersions and sterile powders for the later preparation of sterile injectable solutions or dispersions. For intravenous administration, suitable carriers include physiological saline, bacteriostatic water, Cremophor EL® (BASF; Parsippany, N.J.) or phosphate-buffered saline (PBS). In all cases, the composition must be sterile and should be fluid to the extent that syringability exists. The composition must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol and the like) and suitable mixtures thereof. The proper fluidity can be maintained, for example, by the use of a coating such as lecithin, by the maintenance of the required particle size in the case of dispersion and by the use of thickeners or surfactants. Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols, such as mannitol, sorbitol or sodium chloride in the composition. Prolonged absorption of the injectable compositions can be brought about by including in the composition an agent that delays absorption, for example, aluminum monostearate or gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches or capsules. Oral compositions also can be prepared using a fluid carrier to yield a syrup or liquid formulation, or for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients or compounds of a similar nature: a binder such as microcrystalline cellulose, gum tragacanth or gelatin; an excipient such as starch or lactose; a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate or orange flavoring.

For administration by inhalation, the compound is delivered in the form of, for example, an aerosol spray from a pressurized container or dispenser that contains a suitable propellant, e.g., a gas such as carbon dioxide or a nebulizer, or a mist.

Systemic administration also can be by transmucosal or transdermal means. For transmucosal or transdermal administration, penetrants appropriate to the barrier to be permeated are used in the formulation. Such penetrants generally are known in the art and include, for example, for transmucosal administration, detergents, bile salts and fusidic acid derivatives. Transmucosal administration can be accomplished through the use of nasal sprays or suppositories. For transdermal administration, the active compounds are formulated into ointments, salves, gels or creams as generally known in the art. Another known penetrant is dimethyl sulfoxide.

The compound also can be prepared in the form of suppositories (e.g., with conventional suppository bases such as cocoa butter and other glycerides) or retention enemas for rectal delivery.

In one embodiment, the active compound is prepared with carriers that will protect the compound against rapid elimination from the body, such as a controlled release formulation, including implants, depots, pumps and microencapsulated delivery systems. Biodegradable, biocompatible polymers can be used, such as ethylene vinyl acetate, polyanhydrides, polyglycolic acid, collagen, polyorthoesters and polylactic acid. For example, a formulation can be enteric coated.

Methods for preparation of such formulations will be apparent to those skilled in the art. The materials also can be obtained commercially from Alza Corporation and Nova Pharmaceuticals, Inc.

Liposomal and cochleate suspensions (including liposomes targeted to infected cells with antibodies or other targeting moieties) also can be used as pharmaceutically acceptable carriers. Those can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The dosages, for example, preferred route of administration and amounts, are obtainable based on empirical data obtained from preclinical and clinical studies, practicing methods known in the art. For repeated administrations over several days or longer, depending on the condition, the treatment is sustained until a desired suppression of disease symptoms occurs. However, other dosage regimens may be useful. The progress of the therapy is monitored easily by conventional techniques and assays. An exemplary dosing regimen is disclosed in WO 94/04188. The specification for the dosage unit forms of the invention is dictated by and directly dependent on the unique characteristics of the active compound and the particular therapeutic effect to be achieved and the limitations inherent in the art of compounding such an active compound for the treatment of individuals.

The pharmaceutical compositions can be included in a container, pack or dispenser together with instructions for administration.

Another method of administration comprises the addition of a compound of interest into or with a food or drink, as a food supplement or additive, or as a dosage form taken on a prophylactic basis, similar to a vitamin. The conjugate of interest can be encapsulated into forms that will survive passage through the gastric environment. Such forms are commonly known as enteric-coated formulations. Alternatively, the conjugate of interest can be modified to enhance half-life, such as chemical modification of the peptide bonds, to ensure stability for oral administration, as known in the art.

The instant invention provides for both prophylactic and therapeutic methods of treating a subject at risk of (or susceptible to) cancer. The particular dosages, that is, the amount per dose and the mode of administration, are determined as known in the art, based on the empirical knowledge obtained from use of the active agent alone, pre-clinical studies, indication, clinical studies and the like, following known pharmacologic and pharmaceutical paradigms.

The invention now will be exemplified in the following non-limiting examples.

EXAMPLES

Materials: Random asymmetrically branched polyethyleneimines were purchased from Aldrich and Polysciences. Regular asymmetrically branched polymers were prepared according to procedures provided in U.S. Pat. No. 4,289,872. Colloidal gold particles were prepared according to procedures published in the literature (G. Frens et al., Nature Physical Science, Vol. 241, Jan. 1, 1973, 20). All of the antibodies were purchased from Sigma-Aldrich, Biodesign, or Fitzgerald.

Synthesis of Modified Random Asymmetrically Branched PEIs with Amino Functional Groups (m-ran-AB-PEI-NH$_2$-1.0)

The following reagents including random asymmetrically branched polyethyleneimine (ran-AB-PEI, MW 2,000, 25,000, and 75,000), methyl acrylate (MA, FW=86.09), ethylenediamine (EDA, FW=60.10) and methanol were utilized in this synthesis.

To a round bottom flask were added 1.0 g PEI (MW 2,000) and 20 ml methanol (solution A). To a separate round bottom flask were added 3.0 g methylacrylate (MA) and 10 ml methanol (solution B). Solution A was then slowly dropped into solution B while stirring at room temperature. The resulting solution was allowed to react at 40° C. for 2 hours. On completion of the reaction, the solvent and unreacted MA monomer were removed by rotary evaporation, and the product, MA-functionalized PEI, was then redissolved in 20 ml of methanol.

To a round bottom flask were added 80 g EDA and 50 ml of methanol, followed by a slow addition of MA-functionalized PEI at 0° C. (1 g MA dissolved in 20 ml methanol). The solution was then allowed to react at 4° C. for 48 hours. The solvent and the excess EDA were removed by rotary evaporation. The crude product was then precipitated out from an ethyl ether solution, and further purified by dialysis to give about 3.0 g of primary amine-functionalized random asymmetrically branched PEI (m-ran-AB-PEI-NH$_2$-1.0) with a molecular weight of about 7300. The product was characterized by $^1$H and $^{13}$C nuclear magnetic resonance (NMR), and size exclusion chromatography (SEC).

Other MA or primary amine-modified random asymmetrically branched PEI and regular asymmetrically branched polylysine polymers with various molecular weights were prepared in a similar manner.

Synthesis of Modified Random Asymmetrically Branched PEIs with Mixed Hydroxyl and Amino Functional Groups (m-ran-AB-PEI-NH$_2$/OH-2)

The following reagents including amino-functionalized random asymmetrically branched polyethyleneimine (m-ran-AB-PEI-NH$_2$-1.0), MA, EDA, monoethanolamine (MEA, FW=61.08), and methanol were utilized in this synthesis.

To a round bottom flask were added 1.0 g amino-modified PEI or m-ran-AB-PEI-NH$_2$-1.0 produced from the previous procedure and 20 ml of methanol (solution A). To a separate round bottom flask were added 3.0 g of MA and 10 ml methanol (solution B). Solution A was then slowly dropped into solution B while stirring at room temperature. The resulting solution was allowed to react at 40° C. for 2 hours. On completion of the reaction, the solvent and unreacted monomer MA were removed by rotary evaporation, and the product, MA-functionalized m-ran-AB-PEI-MA-1.5, was then redissolved in 20 ml of methanol.

To a round bottom flask were added 60 g EDA, 240 g MEA and 100 ml methanol (the mole ratio of EDA:MEA is 20:80), followed by slow addition of m-ran-AB-PEI-MA-1.5 at 0° C. (1 g MA dissolved in 20 ml of methanol). The solution was then allowed to react at 4° C. for 48 hours. The solvent and the excess EDA were removed by rotary evaporation. The crude product was then precipitated from an ethyl ether solution, and further purified by dialysis to give about 3.0 g of mixed hydroxyl and amino-functionalized random ABP (m-ran-AB-PEI-NH$_2$/OH-2.0, with an average of 20% NH$_2$ and 80% OH groups and the molecular weight is about 18,000).

Other modified random AB-PEI and regular AB polylysine polymers with various ratios of hydroxyl and amino groups, as well as different molecular weights were prepared in a similar manner.

Synthesis of Alkyl-Modified Random Asymmetrically Branched Poly(2-ethyloxazoline) (PEOX) with Primary Amine Chain End Group The synthesis of CH$_3$—(CH$_2$)$_{178}$-PEOXABP100 (ABP100 is an arbitrary name to denote the ratio of monomer to initiator in the initial reaction) is provided as a general procedure for the preparation of core-shell nanocapsules. A mixture of CH$_3$(CH$_2$)$_{178}$CH$_2$—Br (3.36 g) in 500 ml of toluene was azeotroped to remove water with a distillation head under N$_2$ for about 15 min. 2-Ethyloxazoline (100 g) was added dropwise through an addition funnel, and the mixture was allowed to reflux between 24 and 48 hours. On completion of the polymerization, 12.12 g of EDA were added to the reactive polymer solution (A) to introduce the amine function group. The molar ratio of polyoxazoline chain end to EDA is 1 to 20.

Morpholine also can be added to terminate the reaction. Thus, morpholine was added to the reactive polymer solution (A) to terminate the reaction. The crude product was re-dissolved in methanol and then precipitated out from a large excess of diethyl ether. The bottom layer was re-dissolved in methanol and dried by rotary evaporation and vacuum to give an asymmetrically random core-shell hyper-branched PEOX polymer as a white solid (101 g). Other asymmetrically hyperrandom-branched polymers such as C$_{12}$-PEOX ABP20, 50, 100, 200, 300, 500, C$_{18}$-PEOX ABP20, 50, 200, 300, 500, C$_{22}$-PEOX ABP20, 50, 100, 200, 300, 500, and polystyrene-PEOX etc. as well as non-modified and modified poly(2-substituted oxazoline) such as poly(2-methyl oxazoline) polymers were prepared in a similar manner. All the products were analyzed by SEC and NMR.

Preparation of IgG-Asymmetrical Randomly Branched Polymer Conjugates

The preparation of randomly branched mixed surface (OH/NH$_2$ mix) m-ran-AB-PEI-NH$_2$/OH-2-IgG conjugates is provided as a general procedure for the preparation of polymer-antibody and polymer-streptavidin conjugates. Other conjugates such as PEI-IgG, m-ran-AB-PEI-NH$_2$-1-IgG, m-ran-AB-PEI-NH$_2$-2-IgG, m-ran-AB-PEI-NH$_2$-3-IgG, m-ran-AB-PEI-NH$_2$-4-IgG, as well as m-ran-AB-PEI-NH$_2$/OH-1 (OH/NH$_2$ mix)-IgG, m-ran-AB-PEI-NH$_2$/OH-2 (OH/NH$_2$ mix)-IgG, m-ran-AB-PEI-NH$_2$/OH-3 (OH/NH$_2$ mix)-IgG, regular polylysine polymer, alkyl-modified random branched poly(2-ethyloxazoline) with primary amine chain ends were all synthesized in a similar manner. The synthesis of various protein conjugates with asymmetrically random branched PEOX polymers is also conducted in a similar manner. The biotinylated-IgG conjugates were synthesized as provided in Bioconjugate Techniques (G. Hermanson, Academic Press, 1996).

LC-SPDP-mixed surface m-ran-AB-PEI-NH$_2$/OH-2: To the mixed surface randomly branched m-ran-AB-PEI-NH$_2$/OH-2 (400×10$^{-9}$ mol) in 400 µl of phosphate buffer (20 mM phosphate and 0.1M NaCl, pH 7.5) were added 4.0×10$^{-6}$ mol of sulfo-LC-SPDP (Pierce, Ill.) in 400 µl of water. This was vortexed and incubated at 30° C. for 30 minutes. The LC-SPDP-m-ran-AB-PEI-NH$_2$/OH-2 was purified by gel filtration chromatography and equilibrated with buffer A (0.1 M phosphate, 0.1 M NaCl and 5 mM EDTA, pH 6.8). It was further concentrated to yield 465 μl of solution, with a concentration of approximately 0.77 nmol/μmol.

Thiolated m-ran-AB-PEI-NH$_2$/OH-2 from LC-SPDP m-ran-AB-PEI-NH$_2$/OH-2: The LC-SPDP m-ran-AB-PEI-NH$_2$/OH-2 (50 nmol in 65 ml of buffer A) was mixed with 100 μl of dithiothreitol (DTT) (50 mM in buffer A) and was allowed to incubate at room temperature for 15 minutes. Excess DTT and byproducts were removed by gel filtration with buffer A. It was concentrated in a 10 K Centricon Concentrator to yield 390 μl of the thiolated m-ran-AB-PEI-NH$_2$/OH-2 that was used for conjugation with the activated antibody.

Maleimide R (MAL-R)-Activated Antibody: To the antibody in PBS (310 μL, 5.1 mg or 34 nmol) were added 20.4 ml of a MAL-R-NHS (N-hydroxysuccinimide) solution (10 mM in water). The mixture was vortexed and incubated at 30° C. for 15 minutes. It was purified by gel filtration with buffer A. The maleimide-R-activated antibody was used for conjugation with the thiolated m-ran-AB-PEI-NH$_2$/OH-2.

m-ran-AB-PEI-NH$_2$/OH-2-Antibody Conjugate: To the thiolated m-ran-AB-PEI-NH$_2$/OH-2 (310 μl or 35.7 nmol) was added the MAL-R-activated antibody (4.8 μl or 34 nmol). The reaction mixture was concentrated to approximately 800 μl, which was allowed to incubate overnight at 4° C., and at room temperature for about 1 hr. On completion, the reaction was quenched with 100 μl of ethyl maleimide (50 mmolar solution), and the conjugate was then fractionated on a carboxymethyl cellulose column (5 ml) with a sodium chloride step gradient in 20 mM phosphate buffer at pH 6. The conjugate was eluted with a sodium chloride gradient, and characterized by cationic exchange chromatography, UV spectroscopy, and polyacrylamide gel electrophoresis.

Conjugation via Reductive Coupling

Reduction of Antibody: To the antibody, 2.1 mg or 14 nmol in 160 μL of buffer B (containing 0.1 M sodium phosphate, 5 mM EDTA, and 0.1 M NaCl, pH 6.0) were added 40 μL of DTT (50 mM in buffer B). The solution was allowed to stand at room temperature for 30 min. It was purified by gel filtration in a Sephadex G-25 column equilibrated with buffer B. The reduced antibody was concentrated to 220 μL, and was used for the following conjugation.

MAL-R-Mixed Surface ABP: To the mixed surface ABP in 400 μL (400×10$^{-9}$ mols) at pH 7.4 were added 400 μL of MAL-R-NHS (10 mM in water). This was mixed and incubated at 30° C. for 15 min. On termination, it was purified on a Sephadex G-25 column equilibrated with buffer B. The MAL-R-mixed surface ABP was collected and stored in aliquots in the same buffer at −40° C.

Mixed Surface ABP-Antibody Conjugate: To the reduced antibody (14 nmols in 220 μL) was added the MAL-R-mixed surface m-ran-AB-PEI-NH$_2$/OH-2 (154 μL, 16.6 nmols) with stirring. To this were added 12.5 μL of sodium carbonate (1.0 M solution) to bring the pH to ~6.8. The reaction was continued for 1 hr at room temperature. It was terminated with the addition of 100 μL of cysteamine (0.4 mM solution). The conjugation mixture was purified on a CM cellulose column with a sodium chloride gradient elution.

Colloidal Gold-Based Immunoassays

Preparation of Gold-Ab Conjugates:

To a 125 ml flask were added 60 ml of colloidal gold solution (20-80 nm in diameter as measured by TEM, O.D. 1.078 as measured by UV spectroscopy) (Frens et al., supra). The pH of the solution was adjusted to 8-11 by addition of a 0.2 M potassium carbonate solution. To this solution were added 600 μl of conjugated antibody solution (O.D. 0.1-1.5 in sodium borate buffer) while stirring, followed by subsequent addition of 600 ml of bovine serum albumin (20% with sodium azide stabilizer). The mixture was stirred at 20° C. for 20-60 more minutes. The solution remained purple in color and some foaminess was observed. On completion, the stir bar was removed, and the reaction mixture was transferred to two 50 ml conical tubes. The material was centrifuged until very little color was observed in the supernatant. The supernatant was removed and 400 μl of 25 mM sodium borate buffer were added in each tube. The contents were mixed thoroughly and the two tubes of material were combined and characterized by UV-Vis.

The gold-ABP-streptavidin conjugates were prepared in a similar manner. The gold-ABP-streptavidin-biotin-Ab conjugates were prepared through subsequent addition of biotinylated Ab to gold-ABP-streptavidin conjugates. Other biologically active molecules, which can be used as reporters, such as horseradish peroxidase (HRP) or avidin and derivatives and analogs thereof can also be attached to gold in a similar manner. However, during the test, additional substrates have to be added to achieve signal enhancement.

Lateral Flow or Dipstick Immunoassay Ticket Experiments

An immunoassay device or "ticket" can consist of a strip of cellulose or other membrane (c) in a membrane-retaining device, generally composed of an inert plastic, an adsorbent pad (a) and a receiving pad (b) at the ends of the membrane (FIG. 5A). Two different antibodies (capture (d) and control (e) antibody) are sprayed on the membrane within about a 4 mm distance. The capture antibody is utilized to capture analyte molecules, while the control antibody is utilized to verify the activity of detector antibodies. The detector antibody (labeled with a reporter, for example, previously conjugated on colloidal gold particles) is stored on a conjugate release pad (b), and is placed underneath the adsorbent pad. The strip/pad complex is then placed in a retaining device (FIG. 5B), primarily for the ease of handling in the field or home environment. The total weight of this ticket can be about 4.5 g, and the dimensions can be about 2 cm (width)×7 cm (length)×0.5 cm (thickness).

Once the sample solution is applied on the adsorbent pad (a) through either the sample well or applied using a dipstick, the antigen will mix with the detector antibody-ABP-gold conjugate in situ, and the resulting antigen-detector antibody-ABP-gold complex will be captured by the capture antibody previously sprayed on the membrane. As a result, a complex consisting of capture antibody-antigen-detector antibody-ABP-gold complex is formed, with a red color appearing (T) (FIG. 5B).

This complex is distinctly different from the prior art (i.e., "sandwich" based lateral flow immunoassays), which comprise a different complex or product consisting of only capture antibody-antigen-detector antibody-gold complexes. Within these complexes, the detector antibodies directly interact with colloidal gold particles, thus resulting in random orientation of such antibodies at the gold surface. This random orientation generates undesired precrosslinked products (i.e., detector antibody-colloidal gold particle clusters), significantly raising the background noise or false positive levels. In contrast, the instant ABP-based assays completely eliminate the precrosslinked side products. As a result of this composition difference, the ABP-based assays show a 100-fold sensitivity enhancement with 10-20-fold less reagents (FIG. 6).

As illustrated in FIG. 5B, on applying an unknown solution to the sample well (S), if both capture (T) and control (C) lines turn red, the test result is positive. If only the control line changes to red, the test is negative.

The assay can be configured to be qualitative, that is, the results will be presented in a form and manner that yields in a robust fashion either a positive or a negative result for what the assay is intended to provide with results visually discernable. On the other hand, the assay format is amenable to yielding quantifiable results. Thus, the ticket can be scanned by a device that provides a measure for the level of reaction.

A series of samples with antigen (i.e., toxoid) concentrations ranging from 1-250 ng/ml (in a total volume of 100 ml) were prepared for the test. Once the sample solution is added dropwise over 5 seconds to the adsorbent pad (the time is noted), the solution will flow laterally based on the capillary movement of the fluid phase. The gold-Ab or gold-ABP-Ab conjugate will be released as soon as the solution passes through the conjugate release pad. If the test is positive, both control and test lines will turn red due to the formation of immunocomplexes, and the red color results from the colloidal gold particles. If the test is negative, only the control line will turn red and no color will appear on the test line due to the absence of "sandwich" immunocomplexes at the test line/capture Ab sites. The time required for detection is about 15 minutes.

According to the same assay design, the microarray-based assays can be constructed in a similar manner. In this case, capture antibodies are spotted on a solid surface through commercially available microarray robots, where detector antibody-gold conjugates are mixed together. On the addition of an unknown sample in a direct, indirect, or sequential sandwich assay format, positive tests show red color changes in the corresponding capture antibody locations predetermined on the surface, while the negative tests exhibit no color changes. Alternatively, in a competition assay format, the reverse is true. Again, the polymer of interest is utilized to affix the antibodies or antigens to the solid surface.

All references herein cited, including the two provisional applications from which benefit is claims, U.S. Ser. No. 60/523,692, filed Nov. 21, 2003 and 60/580,728, filed Jun. 21, 2004 are herein incorporated by reference in entirety.

It will be apparent to one skilled in the art that various changes, alterations, and modifications of the present invention are possible in light of the above teachings. It is therefore to be understood that while the invention has been described in this specification with some particularity, it is not intended to limit the invention to the particular embodiments provided herein. On the contrary, it is intended to cover all alternatives, modifications, and equivalents as may be included within the spirit and scope of the invention.

We claim:

1. A kit comprising: (1) a reagent comprising a randomly branched dendritic polymer conjugate which comprises: (a) at least one modified randomly branched dendritic polymer without a core comprising chain branches, terminal branches or both, wherein said randomly branched dendritic polymer is modified to comprise a functional group for branch formation, said randomly branched dendritic polymer comprising random, asymmetric branches and random, asymmetric branch junctions; and covalently conjugated thereto (b) at least one bioactive agent; and (2) a reporter.

2. The kit of claim 1, wherein said randomly branched dendritic polymer connects with another bioactive agent.

3. The kit of claim 1, wherein said randomly branched dendritic polymer comprises a modified polyethyleneimine.

4. The kit of claim 1, wherein said randomly branched dendritic polymer comprises a modified polyoxazoline.

5. The kit of claim 4, wherein said modified polyoxazoline comprises a modified poly(2-methyoxazoline) or a modified poly(2-ethyloxazoline).

6. The kit of claim 1, wherein said randomly branched dendritic polymer comprises a modified polylysine.

7. The kit of claim 1, wherein said bioactive agent comprises a metal.

8. The kit of claim 7, wherein said metal comprises a transition metal, an alkali metal, an alkaline-earth metal, a Lanthanide series element or an Actinide series element.

9. The kit of claim 1, wherein said bioactive agent comprises a member of a binding pair.

10. The kit of claim 9, wherein said binding pair comprises a polynucleotide, an antibody, an antigen-binding portion thereof, an antigen or an epitope-containing portion thereof.

11. The kit of claim 1, wherein said reporter comprises a colored, luminescent or fluorescent particulate or moiety, an enzyme, or a combination thereof.

12. The kit of claim 11, wherein said fluorescent or luminescent particulate or moiety comprises quantum dots, nanocrystals, up-converting phosphorescent particles, a Lanthanide metal or fluorophore containing latex beads.

13. The kit of claim 11, wherein said colored particulate or moiety comprises colloidal metals, comprising gold or silver, colored latex beads or colored dyes.

14. The kit of claim 1, wherein said kit comprises a solid phase comprising said reagent and said reporter.

15. The kit of claim 14, wherein said solid phase comprises a flat surface or a membrane.

16. The kit of claim 15, wherein said flat surface comprises a silicon wafer, quartz, glass, a metal, or a plastic.

17. The kit of claim 15, wherein said membrane comprises a paper, a plastic membrane, a nylon membrane or nitrocellulose.

18. The kit of claim 14, wherein said solid phase and said reagent comprise a microarray or a bead array.

19. The kit of claim 1, wherein said reporter yields a product which is detectable by color or by light.

20. The kit of claim 1, wherein said bioactive agent binds to a biological polymer, a hormone, a neurotransmitter, a pathogen, a toxin, or a drug.

21. The kit of claim 20, wherein said pathogen comprises a bacterium, a spore, a parasite or a virus.

22. The kit of claim 20, wherein said biological polymer comprises a polypeptide, a polysaccharide or a polynucleotide.

23. The kit of claim 22, wherein said polypeptide comprises an enzyme.

24. The kit of claim 22, wherein said polypeptide comprises an antibody, an antigen-binding portion thereof, an antigen or an epitope-containing portion thereof.

25. The kit of claim 14, wherein said solid phase comprises a dipstick, a microtiter plate, a lateral flow immunoassay or a microarray.

26. The kit of claim 1, wherein said bioactive agent comprises a drug.

27. The kit of claim 26, wherein said drug comprises an anesthetic, antibiotic, antifungal, antiviral, analgesic, antihypertensive, anti-inflammatory, antidote, antihistamine, chemotherapeutic agent, antidepressant, depressant, stimulant, tranquilizer, urinary anti-infective, vasoconstrictor, vitamin, cardioactive drug, immunosuppressive, or a nutritional supplement.

28. The kit of claim 26, wherein said drug comprises a biological polymer.

29. The kit of claim 26, wherein said drug comprises a hormone.

30. The kit of claim 28, wherein said biological polymer comprises a polypeptide or a polynucleotide.

31. The kit of claim 30, wherein said polynucleotide comprises a DNA or an RNA.

32. The kit of claim 30, wherein said polypeptide comprises ligand or antigen binding.

33. The kit of claim 32, wherein said antigen binding polypeptide comprises an immunoglobulin or antigen-binding portion thereof.

34. The kit of claim 31, wherein said RNA comprises an RNAi.

35. The kit of claim 1, wherein said polymer comprises a modified polyethylene glycol.

36. The kit of claim 12, wherein said Lanthanide metal is Europium.

37. The kit of claim 14, wherein said solid phase comprises a holder.

38. The kit of claim 37, further comprising identifying information.

39. The kit of claim 38, wherein said identifying information comprises a bar code.

40. The kit of claim 1, wherein said bioactive agent comprises an avidin, an antibody which binds a drug, or both, wherein said drug comprises a digoxin.

41. The kit of claim 1, wherein said bioactive agent comprises a biotin, an antibody which binds a drug, or both, wherein said drug comprises a digoxin.

42. The kit of claim 1, wherein said bioactive agent comprises streptavidin.

43. The kit of claim 1, wherein said bioactive agent comprises colloidal gold.

44. The kit of claim 1, further comprising a a device for detecting said reporter or a product of said reporter.

45. The kit of claim 44, wherein said device is hand-held or portable.

46. The kit of claim 44, wherein said device is a scintillation counter, a Geiger counter, a colorimeter, a refractometer, a reflectometer, a scanner, a charge coupled device or a complementary metal oxide semiconductor device.

* * * * *